United States Patent
Zhang et al.

(10) Patent No.: US 11,939,286 B2
(45) Date of Patent: Mar. 26, 2024

(54) METHOD FOR PRODUCING VINYL ACETATE (71) Applicant: TIANJIN UNIVERSITY, Tianjin (CN)

(72) Inventors: Minhua Zhang, Tianjin (CN);
Zhongfeng Geng, Tianjin (CN); He Dong, Tianjin (CN); Hao Gong, Tianjin (CN); Yingzhe Yu, Tianjin (CN); Shenghua Qian, Tianjin (CN); Xiuqin Dong, Tianjin (CN)

(73) Assignee: TIANJIN UNIVERSITY, Tianjin (CN)

( * ) Notice: Subject to any disclaimer, the term of this patent is extended or adjusted under 35 U.S.C. 154(b) by 0 days.

(21) Appl. No.: 18/023,300

(22) PCT Filed: Sep. 23, 2021

(86) PCT No.: PCT/CN2021/119874
§ 371 (c)(1),
(2) Date: Feb. 24, 2023

(87) PCT Pub. No.: WO2022/083396
PCT Pub. Date: Apr. 28, 2022

(65) Prior Publication Data
US 2023/0312452 A1    Oct. 5, 2023

(30) Foreign Application Priority Data
Oct. 20, 2020   (CN) ......................... 202011127390.0

(51) Int. Cl.
C07C 67/05      (2006.01)
C07C 67/48      (2006.01)
(Continued)

(52) U.S. Cl.
CPC .............. C07C 67/05 (2013.01); C07C 67/48 (2013.01); C07C 67/54 (2013.01); C07C 69/15 (2013.01)

(58) Field of Classification Search
CPC ....... C07C 67/05; C07C 67/54; C07C 67/055; C07C 67/48; C07C 69/15
See application file for complete search history.

(56) References Cited

U.S. PATENT DOCUMENTS 3,905,875 A * 9/1975 Kronig ..................... B01D 3/36
                                                        203/99
4,897,161 A    1/1990 Berg
9,045,413 B2 * 6/2015 Aslam .................. C07C 67/055

FOREIGN PATENT DOCUMENTS

CN         102936198        *  2/2013
CN         102936198 A        2/2013
(Continued)

OTHER PUBLICATIONS

CN102936198, Zhang Mina et al., Vinyl acetate production method, English translation, 14 pages (Year: 2013).*

(Continued)

Primary Examiner — Yate' K Cutliff (57) ABSTRACT

The present disclosure relates to a method for producing vinyl acetate, comprising a vinyl acetate synthesis process, a vinyl acetate refining process and a separation process of vinyl acetate and ethyl acetate, including an acetic acid evaporator, an oxygen mixer, a vinyl acetate synthesis reactor, a first gas separating tower, a second gas separating tower, a recovered gas compressor, a water washing tower, an absorption tower and a desorption tower, a recycling gas compressor; the vinyl acetate refining process comprising an acetic acid tower, a crude VAC tower, and a fine VAC tower, a rectifying tower, an ethyl acetate tower, a water phase receiving tank, an extracting and rectifying tower and an ethyl acetate phase separator.

5 Claims, 3 Drawing Sheets (51) Int. Cl.
      *C07C 67/54*      (2006.01)
      *C07C 69/15*      (2006.01)

(56)              References Cited

FOREIGN PATENT DOCUMENTS

CN        112209830 A      1/2021
GB          1305367    *   1/1973
GB          1305367 A      1/1973

OTHER PUBLICATIONS

International Search Report of PCT/CN2021/119874.
Written Opinion of PCT/CN2021/119874.

* cited by examiner

METHOD FOR PRODUCING VINYL ACETATE

CROSS-REFERENCE TO RELATED APPLICATIONS

This Application is a national stage application of PCT/CN2021/119874. This application claims priorities from PCT Application No. PCT/CN2021/119874, filed Sep. 23, 2021, and from the Chinese patent application 2020111273900 filed Oct. 20, 2020, the content of which are incorporated herein in the entirety by reference.

TECHNICAL FELID

The present disclosure relates to a method and device for producing vinyl acetate, in particular to a method for producing vinyl acetate, which can increase the yield of products, reduce waste emission and decrease the consumption of materials and energy.

BACKGROUND

Vinyl acetate (VAC), also known as ethenyl acetate, is an important organic chemical material. The vinyl acetate can generate polyvinyl alcohol (PVA), vinyl acetate-ethylene copolymer (EVA), polyvinyl acetate (PVAC), vinyl acetate-vinyl chloride copolymer (EVC) and other products through self-polymerization or copolymerization with other monomers. These products are widely applied, and generally can be used in the aspects such as adhesives, sizing agents for paper or fabric, paint, ink, leather processing, emulsifiers, water-soluble membranes and soil conditioners. In 2018, the production capacity of the vinyl acetate in China was about 3.318 million tons per year, accounting for about 40% of the global production capacity, and China was the world's largest producer.

Generally speaking, production process routes of the vinyl acetate include an ethylene method and an acetylene method. Production by the ethylene method is predominant at present in the world. Patent ZL201210385948.4 has disclosed a method for producing vinyl acetate and provided a method for producing vinyl acetate by gas phase oxidation of ethylene. In the process of producing the vinyl acetate by the ethylene method, ethylene, oxygen and acetic acid gas, serving as raw materials, are fed into a reactor to make contact with a catalyst, and react at a pressure of 0.5-1.4 MPa (G) and a temperature of 130-220° C. to generate VAC, water and a small quantity of byproducts, and high-temperature reaction gas enters a gas separating tower after being cooled and condensed at multiple stages, so as to achieve the objective of gas-liquid separation. Unreacted ethylene gas returns to a compressor to be recycled. Mixed liquid of acetic acid, VAC and the like condensed in the gas separating tower is fed to a rectifying procedure after being degassed under reduced pressure. Degassed reaction liquid enters an acetic acid tower to be subjected to acetic acid separation, acetic acid in a tower kettle returns to an acetic acid evaporator in a synthesis procedure to be recycled, a stream at a top of the tower is separated and refined by a crude VAC tower and a fine VAC tower to obtain a VAC product, and byproducts such as acetaldehyde, ethyl acetate and water are separated by an aldehydo-ester concentration tower, an acetaldehyde tower, a de-heavy component tower and a dehydration tower and then discharged from a system.

The ethyl acetate is one of the main byproducts in the process of producing the vinyl acetate by the ethylene method. The intermolecular interaction of the vinyl acetate and the ethyl acetate is high, and their relative volatility is low. In order to remove the ethyl acetate impurities from the product, although the ethylene acetate and the ethyl acetate are separated from each other at a high reflux ratio at the cost of energy consumption at present, they still cannot be separated clearly, and the vinyl acetate is still the main component in the stream for discharging the ethyl acetate impurities, resulting in low product yield and high energy consumption. It is urgent to develop an ethyl acetate removal technology in the production process of the vinyl acetate.

The present disclosure aims at providing a method of producing vinyl acetate, which can improve the product quality and reduce the consumption of materials and energy through process reinforcement and system integration.

SUMMARY

The present disclosure relates to a method for producing vinyl acetate, in particular to a method for producing vinyl acetate by gas phase oxidation of ethylene. The present disclosure aims at providing a method for reinforcing the separation of vinyl acetate from ethyl acetate in the production process of the vinyl acetate.

The method for producing the vinyl acetate by gas phase oxidation of the ethylene involved in the present disclosure includes a vinyl acetate synthesis process, a vinyl acetate refining process and a separation process of vinyl acetate and ethyl acetate. The vinyl acetate synthesis process mainly includes an ethylene recovery tower (117), an acetic acid evaporator (103), an oxygen mixer (106), a vinyl acetate synthesis reactor (107), a first gas separating tower (108), a second gas separating tower (112) and a recycle gas compressor (101), all of which are sequentially connected, wherein the first gas separating tower (108) and the second gas separating tower (112) are connected with a degassing tank (113) and then sequentially connected with a recovered gas compressor (114), a water washing tower (115), an absorption tower (116) and a desorption tower (122). The vinyl acetate refining process mainly includes an acetic acid tower (201), a crude VAC tower (202), and a fine VAC tower (203) which are sequentially connected, an aldehydo-ester concentration tower (204) and an acetaldehyde tower (205) which are sequentially connected to one branch at a top of the crude VAC tower (202), and a water phase receiving tank (207) and a dehydration tower (206) which are sequentially connected to one branch at a top of the acetic acid tower (201) and the other branch at the top of the crude VAC tower (202). The separation process of the vinyl acetate and the ethyl acetate mainly includes an extracting and rectifying tower (401), an extracting and rectifying tower condenser (402), an extracting and rectifying tower supercooler (403), and an extracting and rectifying tower phase separator (404) which are sequentially connected, and an ethyl acetate tower (405), an ethyl acetate tower condenser (406), an ethyl acetate tower supercooler (407) and an ethyl acetate tower phase separator (408) which are sequentially connected to a kettle of the extracting and rectifying tower (401).

In the method for producing the vinyl acetate by gas phase oxidation of the ethylene in the present disclosure, the vinyl acetate is generated by the ethylene, oxygen and acetic acid in the vinyl acetate synthesis reactor (107) under the action of a catalyst. As for the catalyst, catalysts known in the art and used for producing the vinyl acetate by gas phase oxidation of the ethylene, such as a USI catalyst and a Bayer catalyst, may be used. Those skilled in the art understand that other catalysts capable of producing the vinyl acetate by gas phase oxidation of the ethylene may also be used, wherein the Bayer catalyst is preferred. As for the reactor for preparing the vinyl acetate from the ethylene, the oxygen and the acetic acid through the reaction, reactors known in the art and used for producing the vinyl acetate by gas phase oxidation of the ethylene may be used. For example, reactors provided in ZL201210240612.9 and ZL201220336812.X may be used, and a reactor described in Section 9.3.3, Chapter 9, *Ethylene Derivatives Engineering*, Chemical Industry Press, July 1995, may also be used.

One of the raw materials used in the method of the present disclosure is ethylene, which may be transformed from petroleum resources, coal resources or biomass resources.

In the method for producing the vinyl acetate of the present disclosure, only part of the ethylene is transformed in the vinyl acetate reactor, and a large amount of untransformed ethylene needs to be recycled. Fresh ethylene from an ethylene source or ethylene production sections is optionally mixed with the recycled ethylene, and then the mixture is preheated and enters the acetic acid evaporator (103) from a bottom, wherein the mixture may be preheated by gas at an outlet of the vinyl acetate synthesis reactor (107). Acetic acid is sprayed from a top of the acetic acid evaporator (103), the ethylene and the acetic acid are in countercurrent contact in the evaporator, and mixed gas of the ethylene and the acetic acid is led out of the top of the evaporator. The content of the acetic acid in the mixed gas may be controlled by controlling a temperature of the top of the evaporator.

The mixed gas of the ethylene and the acetic acid is preheated first after being led out of the top of the acetic acid evaporator (103). For example, the mixed gas may be heated by the gas at the outlet of the vinyl acetate reactor first and then further heated by vapor. The heated mixed gas is fed into the oxygen mixer (106) to be mixed with oxygen. The oxygen mixer is well known in the art, and various oxygen mixers well known in the art may be adopted.

The mixed gas from the oxygen mixer (106) is fed into the vinyl acetate synthesis reactor (107) from a top. As described above, reactors known in the art and used for producing the vinyl acetate by gas phase oxidation of the ethylene may be used. The vinyl acetate synthesis reactor (107) may be a shell-and-tube fixed-bed reactor. The ethylene, the oxygen and the acetic acid are transformed into the vinyl acetate under the action of the catalyst. As described above, the catalyst may be, for example, the USI catalyst and the Bayer catalyst. According to one implementation solution, palladium and gold serve as active ingredients of the Bayer catalyst; and silica gel usually serves as a carrier. According to one implementation solution, the reaction temperature is about 138° C.-185° C., and the pressure is usually about 785 kPa (gauge pressure). Those skilled in the art understand that the adopted catalyst, carrier, temperature and pressure are not specially required in the method of the present disclosure as long as the vinyl acetate may be prepared from the ethylene, the oxygen and the acetic acid by the gas phase method.

The vinyl acetate synthesis reactor (107) is the shell-and-tube fixed-bed reactor, and pressurized water exists among tubes of the shell-and-tube fixed-bed reactor, which is used for removing reaction heat and generating vapor. According to one implementation solution, in the method for producing the vinyl acetate of the present disclosure, the shell-and-tube fixed-bed reactor generates the vapor at the initial stage of operation, and the generated vapor can be used for separating and refining reaction products.

Gas obtained after the reaction also contains a large amount of unconverted ethylene and acetic acid, carbon dioxide, water, oxygen, nitrogen and the like in addition to the target product of vinyl acetate. The large amount of unconverted ethylene must be recycled as the conversion per pass of the ethylene is low in the synthesis process of the vinyl acetate. The reacted gas emitted out of the reactor may be subjected to heat exchange with raw material gas by a first reaction gas cooler (capable of being used for heating mixed gas of ethylene and acetic acid) and a second cooler (capable of being used for heating fed ethylene gas) first to recover heat given off by the product gas at the outlet of the reactor for cooling.

In order to reduce the water content in reaction liquid fed into the rectifying section and reduce the rectifying energy consumption, the first gas separating tower (108) is arranged to pre-dehydrate the reaction liquid by waste heat of the reaction product gas. Specifically, the high-temperature reaction gas at the outlet of the reactor is fed into a bottom of the first gas separating tower (108) after being subjected to heat exchange with low-temperature reaction gas fed into the reactor in the first cooler and the second cooler to be subjected to mass and heat transfer with reflux liquid in the tower, and reaction liquid with water content reduced after pre-dehydration in a tower kettle is fed to the acetic acid tower (201) at the rectifying section to be treated after being depressurized by the degassing tank (113). Overhead vapor mainly consists of vinyl acetate and water, is further cooled after being condensed, and is fed into the phase separator for phase separation, an oil phase obtained after phase separation is fed into the first gas separating tower (108) as reflux, and a water phase is extracted and fed to the water phase receiving tank (207) at the rectifying section.

The overhead vapor of the first gas separating tower (108) is condensed by the air condenser, so as to further reduce the recycling volume and the consumption of recycled water. According to one implementation solution, a temperature of a condensate outlet of the air condenser is 70° C.-110° C. The air condenser is a cooler taking ambient air as a cooling medium, called "air cooler" for short. Various known air condensers may be used herein. Those skilled in the art know and grasp how to select a proper air condenser to meet cooling requirements. For example, in one type of air condenser, an impeller is driven by power to rotate, generated eddy currents continuously draw in air, and cold air makes contact with a hot pipeline and then transfers heat, so that high-temperature process fluid in the pipe is cooled or condensed. For example, the refrigerating capacity of the air cooler may be adjusted by arranging a variable-frequency motor and adjusting angles of fan blades. A common air cooler mainly consists of a tube bundle, an air blower and a framework. For example, structure and property requirements and the like of the air coolers are described in detail in National Standard GB/T 15386-94.

The reaction gas treated by the first gas separating tower (108) still contains a large quantity of non-condensible components, such as ethylene and oxygen, so that acetic acid and vinyl acetate are hardly condensed completely only by an indirect cooling method. If they are not completely separated, the recycled ethylene may contain the acetic acid, and the presence of even a trace amount of acetic acid will cause corrosion of the recycle gas compressor (101). Thus, generally, direct cooling equipment, namely the second gas separating tower (112), should be used in production of the vinyl acetate.

After the reaction gas is condensed by the air condenser as described above, uncondensed reaction gas enters a lower section of the second gas separating tower (112). The second gas separating tower (112) is divided into an upper section, a middle section and the lower section. Tower kettle reaction liquid cooled by the recycled water circulates in the lower section and is in countercurrent contact with ascending gases such as ethylene, carbon dioxide, acetic acid and vinyl acetate, so as to condense the acetic acid gas contained therein; reaction liquid cooled by low-temperature water (such as frozen brine and a methanol aqueous solution) circulates in the middle section and is in countercurrent contact with the ascending gas, so as to condense high-boiling-point substances such as the acetic acid and the vinyl acetate contained therein; and the acetic acid is used for leaching the gas in the upper section, so as to further remove the vinyl acetate from the reaction gas.

After the tower bottoms of the second gas separating tower (112) are cooled by the first cooler of the second gas separating tower, one part of the tower bottoms enter a top of the lower section of the separating tower, the other part of the tower bottoms are further cooled by low-temperature water in the second cooler of the second gas separating tower and then enters a top of the middle section of the second gas separating tower (112), and the two parts of the tower bottoms are in direct countercurrent contact with the ascending gas respectively to condense the acetic acid and the VAC in the gas phase, so that the acetic acid and the VAC are removed from the reaction gas.

The first cooler of the second gas separating tower (112) is a plate heat exchanger or a double-shell-pass shell-and-tube heat exchanger, such as a double-shell-pass fixed shell-and-tube heat exchanger. It is believed that the double-shell-pass shell-and-tube heat exchanger achieves full countercurrent operation of cold and hot media without being limited by any theory, thereby saving cooling water. Any double-shell-pass shell-and-tube heat exchanger or double-shell-pass fixed shell-and-tube heat exchanger known in the art may be used as long as it can achieve a needed cooling effect. Those skilled in the art know and grasp how to select a proper double-shell-pass shell-and-tube heat exchanger or double-shell-pass fixed shell-and-tube heat exchanger to meet cooling requirements. As commonly known to those skilled in the art, a partition plate is put in a center of a tube bundle of the double-shell-pass shell-and-tube heat exchanger, so that a baffle plate is vertically separated, and one shell pass is divided into two parts. As a shell is divided into two parts by the partition plate in the middle, the cold and hot media can be subjected to heat exchange under a pure countercurrent condition, and heat transfer efficiency is far higher than that of a single-shell-pass shell-and-tube heat exchanger. It is believed that the plate heat exchanger achieves full countercurrent, without being limited by any theory, thereby increasing a heat exchange temperature difference and reducing the use amount of the cooling water. The plate heat exchanger is a novel efficient heat exchanger formed by stacking a series of metal sheets with a certain corrugated shape. Thin rectangular channels are formed among the sheets, and heat exchange is performed by the sheets. A heat transfer coefficient of the plate heat exchanger is much higher compared with a conventional shell-and-tube heat exchanger. The plate heat exchanger has a large logarithmic mean temperature difference and a small terminal temperature difference, so that full countercurrent heat exchange can be achieved. Any plate heat exchanger known in the art may be used as long as it can achieve the needed cooling effect. Those skilled in the art know and grasp how to select a proper plate heat exchanger.

Removal of the high-boiling-point components such as the acetic acid and vinyl acetate of the gas from the top of the second gas separating tower (112) is achieved; and the gas mainly consists of the ethylene, the carbon dioxide and the oxygen. Generally, after the gas is compressed by the recycle gas compressor (101), most of the gas circulates and returns to the vinyl acetate synthesis reactor (107); a fraction of side stream gas is additionally extracted to remove inert components such as the carbon dioxide, so as to ensure that an ethylene concentration is not decreased by the accumulation of the inert components, thereby achieving the smooth synthesis reaction.

Generally, the reaction liquid (the mixed liquid of the acetic acid and the vinyl acetate) is continuously extracted from a tower kettle of the second gas separating tower (112) and fed to the degassing tank (113). Gas dissolved in a liquid phase is desorbed under reduced pressure, the gas compressed by the recovered gas compressor (114) is merged with the side stream gas which is compressed by the recycle gas compressor (101) and then subjected to removal of the carbon dioxide, and the merged gas is fed into the water washing tower (115).

Generally, the gas fed into the water washing tower (115) is washed with water, the gas is fed into the absorption tower (116) after the acetic acid and acetaldehyde contained therein are removed, so as to absorb the carbon dioxide therein with a hot potassium carbonate aqueous solution, and most of the gas from a top of the absorption tower (116) is fed to the recycle gas compressor and circulates to the synthesis reactor after being pressurized; a small part of the gas is fed to the rectifying unit as a polymerization inhibitor and a corrosion remover; and the rest is fed to the ethylene recovery tower (117) to recover the ethylene therein and then exhausted to a torch to be burnt out, so as to balance inert gas in the reaction system. Absorption liquid at a bottom of the absorption tower (116) may be fed to the desorption tower (122), and the carbon dioxide is desorbed under depressurization and heating conditions and exhausted out of the desorption tower (122); and the desorbed potassium carbonate solution returns to the absorption tower (116) again as the absorption liquid, and the above system is called a recycle gas decarbonization system.

According to the method for producing the vinyl acetate of the present disclosure, it is beneficial to stabilizing the production process by controlling the proper content of the inert gas in the recycled gas. Specifically, with a control over a certain content of the inert gas, an explosion lower limit of the oxygen may be increased, a stable area of the reaction system may be widened, and an oxygen concentration of the reaction system may be increased, thereby reducing a reaction temperature, prolonging the service life of the catalyst and improving the selectivity of the vinyl acetate. A conventional method in the art is as follows: a decarbonization degree is controlled by the recycle gas decarbonization system, so that the carbon dioxide is kept at a certain concentration in the system, thereby achieving a stabilizing effect. However, the carbon dioxide has a high molecular weight, and its total mass is high under the condition of reaching the same volume fraction, resulting in the high power consumption of the recycle gas compressor (101). Through vapor-liquid phase equilibrium analysis, an inventor found that an absorbent for recovering the ethylene could well absorb impurity component ethane brought in by the raw material gas. Considering that the molecular weight of the ethane is smaller than that of the carbon dioxide, the power consumption is lower when the same stabilizing effect is achieved. Based on the above findings, the inventor proposed a method for taking the ethane brought in by the raw material as a stabilizer and developed a new process taking the ethane as the stabilizer on this basis. Specifically, refined gas fed from the decarbonization system is fed into the ethylene recovery tower (117), and nitrogen therein is exhausted after the ethylene gas and the ethane gas are recovered through the proper absorbent, preferably, the acetic acid. In order to adjust the ethane content in the recycled gas, before the refined gas fed from the decarbonization system is fed into the ethylene recovery tower (117), a branched stream is set for impurity removal, and the ethane content is adjusted by adjusting the quantity of the stream for impurity removal.

As understood by those skilled in the art, vinyl acetate synthetic reaction liquid also contains acetic acid, water, low-boiling-point components and high-boiling-point components in addition to vinyl acetate. After part of a liquid mixture with a significant difference in boiling points of all components is vaporized at a certain temperature, a composition of a gas phase thereof differs from a composition of a liquid phase, and a proportion of volatile substances in the gas phase is more than that of volatile substances in the liquid phase, so that the liquid mixture can be separated and purified by a rectifying method. In vinyl acetate rectifying, all components in the reaction liquid are separated through a series of rectifying operations by means of the difference in relative volatility among the components.

The vinyl acetate refining process of the method for producing the vinyl acetate provided by the present disclosure includes the acetic acid tower (201), the crude VAC tower (202), and the fine VAC tower (203) which are sequentially connected, the aldehydo-ester concentration tower (204) and the acetaldehyde tower (205) which are sequentially connected to one branch at the top of the crude VAC tower (202), and the water phase receiving tank (207) and the dehydration tower (206) which are sequentially connected to one branch at the top of the acetic acid tower (201) and the other branch at the top of the crude VAC tower (202).

The reaction liquid from the degassing tank (113) at the vinyl acetate synthesis section is fed into the acetic acid tower (201) as a feed. The acetic acid is recovered from a bottom of the tower, most of the acetic acid is fed to the acetic acid evaporator (103) at the vinyl acetate synthesis section, and the rest is fed to the second gas separating tower (112) and the water washing tower (115) respectively as acetic acid for leaching.

Vapor is led out of a top of the acetic acid tower (201), which mainly consists of vinyl acetate and water. The vapor is fed to a phase separation tank of the acetic acid tower (201) for layering after being condensed by the condenser. One part of an organic phase on an upper layer refluxes, the other part of the organic phase is extracted and fed to the crude VAC tower (202), and a water phase on a lower layer is fed to the water phase receiving tank (207).

Part of the organic phase of the phase separation tank of the acetic acid tower is fed to the crude VAC tower (202). The crude VAC tower (202) is a rectifying tower used for separating out water and low-boiling-point impurities dissolved in the vinyl acetate. Vinyl acetate not containing low-boiling-point substances is taken out of a tower kettle of the crude VAC tower (202) and fed to the fine VAC tower (203).

Water, low-boiling-point components and a small amount of vinyl acetate are distilled out of a top of the crude VAC tower (202) and enter a phase separation tank of the crude VAC tower (202) for layering after being condensed by the condenser. The vinyl acetate and the low-boiling-point components serve as an organic phase on an upper layer, one part of the organic phase refluxes, and the other part is fed to the aldehydo-ester concentration tower (204); and a water phase on a lower layer is fed to the water phase receiving tank (207) to recover VAC therein.

A condensate cooler of the crude VAC tower is a plate heat exchanger or double-shell-pass shell-and-tube heat exchanger, preferably, the plate heat exchanger. Any plate heat exchanger or double-shell-pass shell-and-tube heat exchanger known in the art may be used as long as it can achieve the needed cooling effect. Those skilled in the art know and grasp how to select a proper plate heat exchanger or double-shell-pass shell-and-tube heat exchanger. For example, the same plate heat exchanger or double-shell-pass shell-and-tube heat exchanger as described above may be adopted. It is believed that after the plate heat exchanger or double-shell-pass shell-and-tube heat exchanger is adopted, full countercurrent can be achieved, the heat exchange temperature difference can be increased, and the use amount of the cooling water can be reduced.

Tower bottoms of the crude VAC tower (202) are fed to the fine VAC tower (203). The fine VAC tower (203) is used for removing high-boiling-point components. Vinyl acetate product vapor is distilled out of a top of the fine VAC tower (203), and may be fed into a storage tank after being condensed and cooled. The tower bottoms are vinyl acetate and high-boiling-point components, which are fed to the acetic acid tower (201).

Feed of the aldehydo-ester concentration tower (204) is the organic phase separated out of the phase separation tank of the crude VAC tower. Low-boiling-point components mainly consisting of acetaldehyde are distilled out of a top of the aldehydo-ester concentration tower (204), after the low-boiling-point components are condensed and cooled, one part refluxes, and the other part is fed to the acetaldehyde tower (205); and tower bottoms mainly contain vinyl acetate, and are fed to the crude VAC tower (202) for refluxing at the tower top. Pure acetaldehyde is distilled out of a top of the acetaldehyde tower (205), for example, the concentration can reach at least 99%. Byproduct acetaldehyde is obtained after the pure acetaldehyde is condensed by the condenser. Light impurity components remains in a tower kettle of the acetaldehyde tower (205), and are fed to a waste liquid treatment device for treatment.

A certain amount of vinyl acetate is dissolved in water separated from the water phases on the lower layers of the phase separation tank of the acetic acid tower and the phase separation tank of the crude VAC tower. In order to recover the vinyl acetate, this part of materials are fed to the water phase receiving tank (207) and fed to the dehydration tower (206), a constant boiling mixture of the vinyl acetate and the water is distilled out of a top of the tower, and the constant boiling mixture returns to the phase separation tank of the crude VAC tower for layering after being condensed by the condenser. Tower bottoms of the dehydration tower (206) are water barely containing the vinyl acetate, which are discharged after waste water treatment.

The water phase materials separated out of the water phases on the lower layers of the phase separation tank of the acetic acid tower and the phase separation tank of the crude VAC tower enter the water phase receiving tank (207) after being preheated. The water phase materials are preheated by the tower bottoms of the dehydration tower (206), wherein the water phase materials are preheated by the plate heat exchanger or double-shell-pass shell-and-tube heat exchanger, preferably, the plate heat exchanger. Any plate heat exchanger or double-shell-pass shell-and-tube heat exchanger known in the art may be used as long as it can achieve the needed cooling effect. Those skilled in the art know and grasp how to select a proper plate heat exchanger or double-shell-pass shell-and-tube heat exchanger. For example, the same plate heat exchanger or double-shell-pass shell-and-tube heat exchanger as described above may be adopted. It is believed that by the adoption of the plate heat exchanger or the double-shell-pass shell-and-tube heat exchanger, full countercurrent operation of the cold and hot media is achieved, the heat exchange temperature difference is increased, the feed temperature is increased, and the use amount of fresh vapor of a reboiler of the dehydration tower (206) is reduced.

The inventor found that ethyl acetate was enriched on a lower portion of the acetic acid tower (201) according to simulation results of a computer throughout the process. Thus, the inventor proposed that a sideline extraction opening was formed in the lower portion of the acetic acid tower (201), through which a concentrate stream of the ethyl acetate was extracted at sidelines. Through the strict computer simulation computation result, the inventor proved that the stream mainly consists of acetic acid, vinyl acetate, water and ethyl acetate. Wherein intermolecular interaction between the vinyl acetate and the ethyl acetate is high, and their relative volatility is low, so that the vinyl acetate and the ethyl acetate cannot be clearly separated even at a large reflux ratio by a conventional rectifying method. The inventor proposed to find an extractant that could change the interaction between the components of the vinyl acetate and the ethyl acetate as a separation strengthening medium to strengthen the separation process, based on which, the inventor used computational quantum mechanics to study molecular structure properties of the vinyl acetate and the ethyl acetate, and found the third component, namely acetic acid, which could change the interaction between the components. Based on the findings of the above basic research, the inventor established a strict mathematical model of an extracting and rectifying tower system and an ethyl acetate tower system, carried out whole flow computation simulation, developed an extracting, rectifying and separating process of vinyl acetate and ethyl acetate with the acetic acid as the extractant, and put forward a method and equipment for removing the ethyl acetate from the vinyl acetate by using the acetic acid as the extractant.

Particularly, main equipment of the separation process of vinyl acetate and ethyl acetate provided by the present disclosure includes the extracting and rectifying tower (401), the extracting and rectifying tower condenser (402), the extracting and rectifying tower supercooler (403), the extracting and rectifying tower phase separator (404), the ethyl acetate tower (405), the ethyl acetate tower condenser (406), the ethyl acetate tower supercooler (407) and the ethyl acetate tower phase separator (408).

A top of the extracting and rectifying tower (401) is sequentially connected with the extracting and rectifying tower condenser (402), the extracting and rectifying tower supercooler (403) and the extracting and rectifying tower phase separator (404), two branches are arranged at an oil phase outlet of the extracting and rectifying tower phase separator (404) and return to the extracting and rectifying tower (401) and the acetic acid tower (201) of the former system respectively, and a water phase outlet is connected with the water phase receiving tank (207). A tower kettle of the extracting and rectifying tower (401) is connected with the ethyl acetate tower (405), a top of the ethyl acetate tower (405) is sequentially connected with the ethyl acetate tower condenser (406), the ethyl acetate tower supercooler (407) and the ethyl acetate tower phase separator (408), a water phase outlet of the ethyl acetate tower phase separator (408) is connected with the ethyl acetate tower (405), and materials at an oil phase outlet are fed out of the system. Two branches are arranged at a tower kettle outlet of the ethyl acetate tower (405) and connected with the extracting and rectifying tower and the acetic acid tower (201) of the former system respectively.

The stream containing acetic acid, vinyl acetate, water and ethyl acetate extracted from the acetic acid tower (201) at the sidelines enters a middle of the extracting and rectifying tower (401), and the acetic acid is adopted as the extractant to be fed on an upper portion of the extracting and rectifying tower (401). The overhead vapor of the extracting and rectifying tower (401) mainly consists of vinyl acetate and water and also contains a trace amount of ethyl acetate not completely removed, condensate condensed by the extracting and rectifying tower condenser (402) enters the extracting and rectifying tower supercooler (403) to be further cooled and then fed into the extracting and rectifying tower phase separator (404) for phase separation, an oil phase part obtained after phase separation refluxes, the rest part is extracted and fed to the acetic acid tower (201) of the former system for treatment, and a water phase is fed to the dehydration tower (206) to recover organic matters therein.

A mixture containing ethyl acetate, a small amount of water and acetic acid in the tower kettle of the extracting and rectifying tower (401) enters the ethyl acetate tower (405) for rectifying. Overhead vapor of the ethyl acetate tower (405) mainly consists of ethyl acetate and water and also contains a trace amount of vinyl acetate, condensate condensed by the ethyl acetate tower condenser (406) enters the ethyl acetate tower supercooler (407) to be further cooled and then fed into the ethyl acetate tower phase separator (408) for phase separation, a water phase obtained after phase separation refluxes, and an oil phase is discharged out of the system as an ethyl acetate impurity stream. A main component in the tower kettle of the ethyl acetate tower (405) is acetic acid, one part of which returns to the extracting and rectifying tower (401) as the extractant, and the rest part returns to the acetic acid tower (201) of the former system for feeding.

The acetic acid is adopted as the extractant in the separation process of the vinyl acetate and the ethyl acetate by adopting the extracting and rectifying process, and the extractant is added from the upper portion of the extracting and rectifying tower (401).

Preferably, the extractant of acetic acid adopts acetic acid brought in the stream extracted from the acetic acid tower (201) at the sidelines and refined by the ethyl acetate tower (405).

A ratio of mass flow of the extractant of acetic acid to mass flow of feed extracted from the acetic acid tower (201) at the sidelines is 0.2-2:1.

Preferably, the ratio of mass flow of the extractant of acetic acid to mass flow of the feed extracted from the acetic acid tower (201) at the sidelines is 1.2:1.

The present disclosure has the beneficial technical effects that by adopting the acetic acid as the extractant, the interaction between the vinyl acetate and the ethyl acetate is changed, the relative volatility of the both is increased, and the content of the vinyl acetate in the stream from which the ethyl acetate impurities are removed is reduced from 90% or above to below 5%, so that the consumption of materials is significantly reduced. The adopted extractant is the acetic acid contained originally in the feed stream, and no new component is introduced, so that a task of treating the extractant in the system is not added after the separating efficiency is improved. By means of the process, the operating cost of the device is greatly reduced.

Where: 103—acetic acid evaporator, 106—oxygen mixer, 107—vinyl acetate synthesis reactor, 108—first gas separating tower, 112—second gas separating tower, 113—degassing tank, 115—water washing tower, 116—absorption tower, 122—desorption tower, 117—ethylene recovery tower, 101—recycle gas compressor, 114—recovered gas compressor, 201—acetic acid tower, 202—crude VAC tower, 203—fine VAC tower, 204—aldehydo-ester concentration tower, 205—acetaldehyde tower, 206—dehydration tower, 207—water phase receiving tank, 401—extracting and rectifying tower, 405—ethyl acetate tower, 402—extracting and rectifying tower condenser, 403—extracting and rectifying tower supercooler, 404—extracting and rectifying tower phase separator, 406—ethyl acetate tower condenser, 407—ethyl acetate tower supercooler, and 408—ethyl acetate tower phase separator.

DETAILED DESCRIPTION OF THE PRESENT DISCLOSURE

A method and device for removing ethyl acetate in the production process of vinyl acetate provided by the present disclosure mainly include an extracting and rectifying tower system and an ethyl acetate tower (405) system. The method and device of the present disclosure are described below with reference to the drawings.

Figure 1:
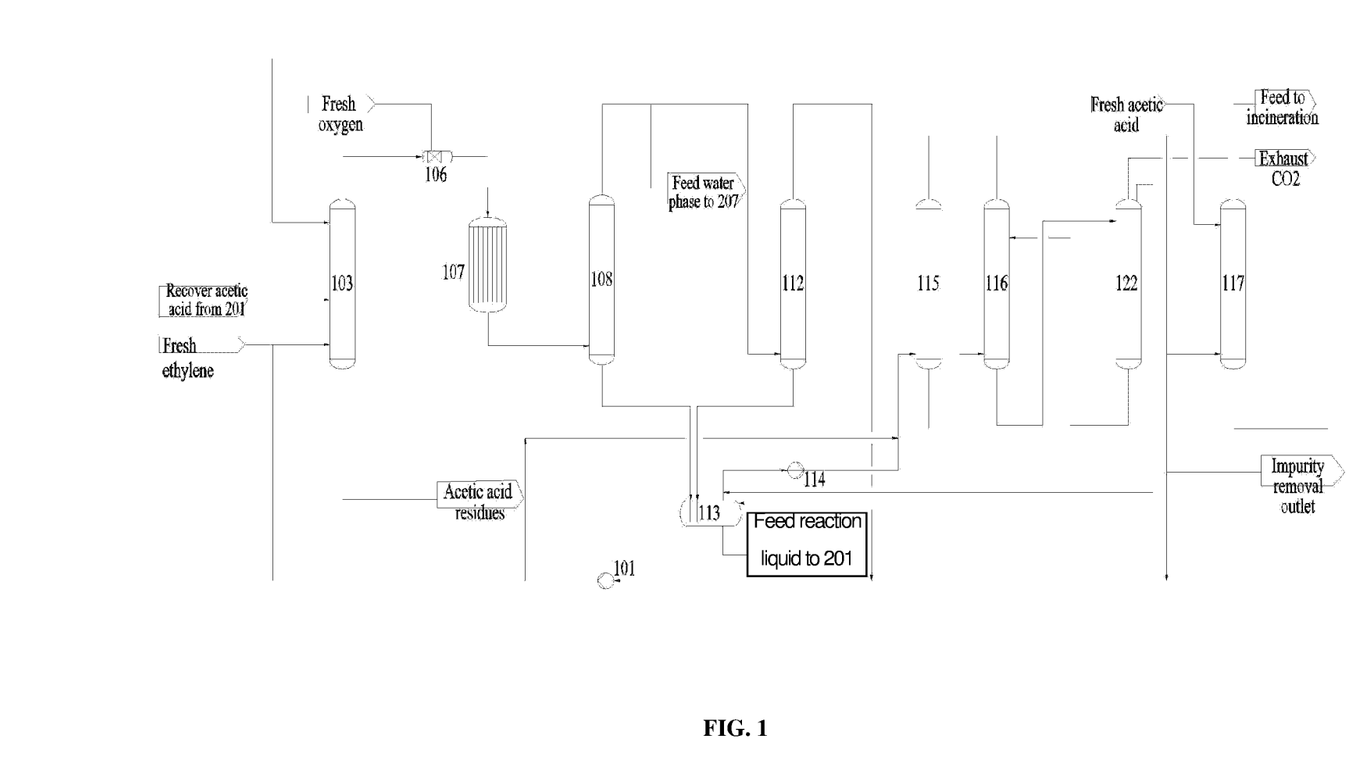
FIG. 1 is a flow schematic diagram of a vinyl acetate synthesis section according to the present disclosure.
Figure 2:
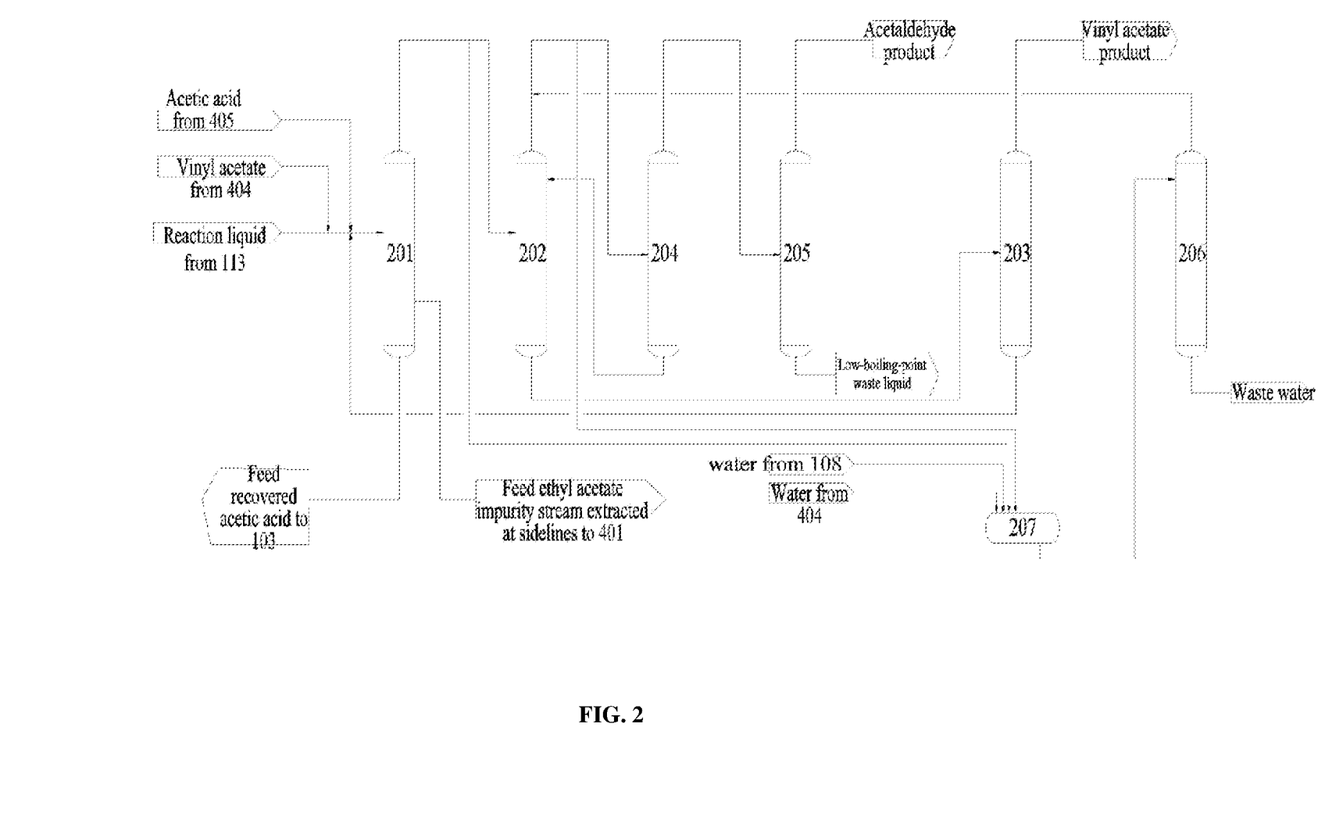
FIG. 2 is a flow schematic diagram of a vinyl acetate rectifying section according to the present disclosure.
Figure 3:
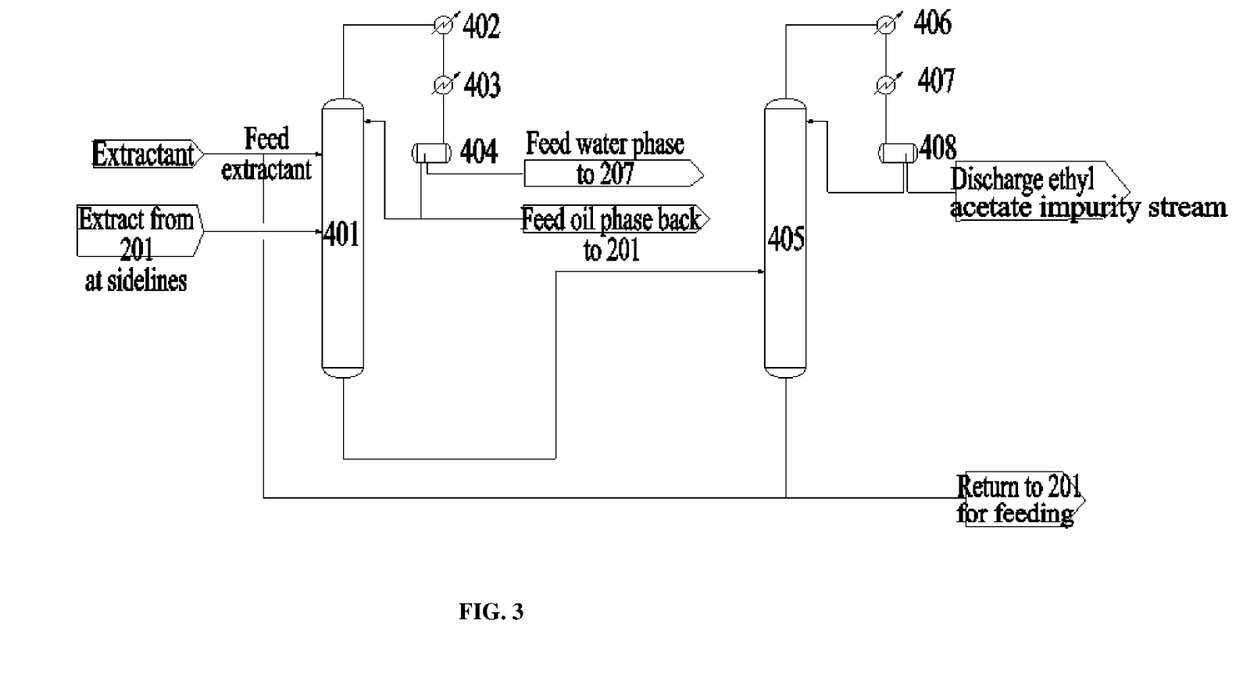
FIG. 3 is a flow schematic diagram of extraction, rectification and separation of vinyl acetate and ethyl acetate according to the present disclosure.

The present disclosure is achieved through methods shown in FIG. 1, FIG. 2 and FIG. 3.

Specifically, after fresh ethylene and recycled gas from a recycle gas compressor (101) are mixed, the mixture enters a lower portion of an acetic acid evaporator (103) and is in countercurrent contact with recycled acetic acid from an acetic acid tower (201) at a rectifying section and fresh acetic acid from an ethylene recovery tower (117). After mixed gas of ethylene and acetic acid obtained from a top of the acetic acid evaporator (103) is further mixed with fresh oxygen in an oxygen mixer (106), the mixture enters a vinyl acetate synthesis reactor (107), a reaction product sequentially enters a first gas separating tower (108) and a second gas separating tower (112) for vapor-liquid separation after being cooled, and the separated gas is boosted by a recycle gas compressor (101) and then returns to the acetic acid evaporator (103) to be recycled. A water phase of condensate at a top of the first gas separating tower (108) is fed to a water phase receiving tank (207). After both tower bottoms of the first gas separating tower (108) and tower bottoms of the second gas separating tower (112) are fed into a degassing tank (113) to be depressurized, deaerated gas is boosted by a recovered gas compressor (114), then converges with side stream gas behind the recycle gas compressor (101), and is fed to a water washing tower (115) and an absorption tower (116) for treatment, wherein a main part returns to an inlet of the recycle gas compressor (101), one part is in countercurrent contact with fresh acetic acid in the ethylene recovery tower (117), and the other part is directly emitted. Tower bottoms of the absorption tower (116) are flashed first before being fed to a desorption tower (122) for desorption, and flash gas is fed to the degassing tank (113) to recover ethylene therein. $CO_2$ is exhausted from a top of the desorption tower (122). A liquid phase of the degassing tank (113) is fed to the acetic acid tower (201) at the rectifying section as reaction liquid.

Reaction liquid from a reaction section enters the acetic acid tower (201) to be separated, acetic acid in a tower kettle is fed to the acetic acid evaporator (103) at a synthesis section to be recycled, and materials at the top of the tower are separated by a crude VAC tower (202) and a fine VAC tower (203) sequentially, so as to obtain a vinyl acetate product. An oil phase material at a top of the crude VAC tower (202) is refined by an aldehydo-ester concentration tower (204) and an acetaldehyde tower (205), so as to obtain an acetaldehyde product and low-boiling-point waste liquid. A water phase of condensate at tops of the acetic acid tower (201) and the crude VAC tower (202) is fed to the water phase receiving tank (207), a material of the water phase receiving tank (207) is fed to a dehydration tower (206), so as to distill out organic matters to be fed back to the crude VAC tower (202), and waste water exists in a tower kettle. An impurity stream containing ethyl acetate is extracted from a lower portion of the acetic acid tower (201) at sidelines to be separated at an extracting and rectifying tower (401).

Preferably, main equipment for separating the vinyl acetate from the ethyl acetate includes the extracting and rectifying tower (401), an extracting and rectifying tower condenser (402), an extracting and rectifying tower supercooler (403), an extracting and rectifying tower phase separator (404), an ethyl acetate tower (405), an ethyl acetate tower condenser (406), an ethyl acetate tower supercooler (407) and an ethyl acetate tower phase separator (408).

A top of the extracting and rectifying tower (401) is sequentially connected with the extracting and rectifying tower condenser (402), the extracting and rectifying tower supercooler (403) and the extracting and rectifying tower phase separator (404), two branches are arranged on an oil phase outlet of the extracting and rectifying tower phase separator (404) and return to the extracting and rectifying tower (401) and the acetic acid tower (201) of the former system respectively, and a water phase outlet is connected with the water phase receiving tank (207). A tower kettle of the extracting and rectifying tower (401) is connected with the ethyl acetate tower (405), a top of the ethyl acetate tower (405) is sequentially connected with the ethyl acetate tower condenser (406), the ethyl acetate tower supercooler (407) and the ethyl acetate tower phase separator (408), a water phase outlet of the ethyl acetate tower phase separator is connected with the ethyl acetate tower (405), and materials at an oil phase outlet are fed out of the system. Two branches are arranged at a tower kettle outlet of the ethyl acetate tower (405) and connected with the extracting and rectifying tower (401) and the acetic acid tower (201) of the former system respectively.

The stream containing acetic acid, vinyl acetate, water and ethyl acetate, which is extracted from the acetic acid tower (201) at the sidelines, enters a middle of the extracting and rectifying tower (401), and the acetic acid is fed from an upper portion of the extracting and rectifying tower (401). The overhead vapor of the extracting and rectifying tower (401) mainly consists of vinyl acetate and water and also contains a trace amount of ethyl acetate not completely removed, condensate condensed by the extracting and rectifying tower condenser (402) enters the extracting and rectifying tower supercooler (403) to be further cooled and then fed into the extracting and rectifying tower phase separator (404) for phase separation, an oil phase part obtained after phase separation refluxes, the rest part is extracted and fed to the acetic acid tower (201) of the former system for treatment, and a water phase is fed to the dehydration tower (206) to recover organic matters therein.

A mixture containing ethyl acetate, a small amount of water and acetic acid in the tower kettle of the extracting and rectifying tower (401) enters the ethyl acetate tower (405) for rectifying. Overhead vapor of the ethyl acetate tower (405) mainly consists of ethyl acetate and water and also contains a trace amount of vinyl acetate, condensate condensed by the ethyl acetate tower condenser (406) enters the ethyl acetate tower supercooler (407) to be further cooled and then fed into the ethyl acetate tower phase separator (408) for phase separation, a water phase obtained after phase separation refluxes, and an oil phase is discharged out of the system as an ethyl acetate impurity stream. A main component in the tower kettle of the ethyl acetate tower (405) is acetic acid, one part of which returns to the extracting and rectifying tower (401) as the extractant, and the rest part returns to the acetic acid tower (201) of the former system for feeding.

The acetic acid is adopted as the extractant in the separation process of the vinyl acetate and the ethyl acetate by adopting the extracting and rectifying process, and the extractant is added from the upper portion of the extracting and rectifying tower (401).

Preferably, the extractant of acetic acid adopts acetic acid brought in the stream extracted from the acetic acid tower (201) at the sidelines and refined by the ethyl acetate tower (405).

A ratio of mass flow of the extractant of acetic acid to mass flow of feed extracted from the acetic acid tower (201) at the sidelines is 0.2-2:1.

Preferably, the ratio of mass flow of the extractant of acetic acid to mass flow of the feed extracted from the acetic acid tower (201) at the sidelines is 1.2:1.

The present disclosure has the beneficial technical effects that by adopting the acetic acid as the extractant, the interaction between the vinyl acetate and the ethyl acetate is changed, the relative volatility of the both is increased, and the content of the vinyl acetate in the stream from which the ethyl acetate impurities are removed is reduced from 90% or above to below 5%, so that the consumption of materials is significantly reduced. The adopted extractant is the acetic acid contained originally in the feed stream, and no new component is introduced, so that a task of treating the extractant in the system is not added after the separating efficiency is improved. By means of the process, the operating cost of the device is greatly reduced.

As an embodiment of the present disclosure, the extractant of acetic acid adopts acetic acid brought in the stream extracted from the acetic acid tower (201) at the sidelines and refined by the ethyl acetate tower (405). A ratio of mass flow of the extractant to mass flow of feed extracted from the acetic acid tower (201) at the sidelines is 1.2:1.

By adopting the acetic acid as the extractant, the interaction between the vinyl acetate and the ethyl acetate is changed, the relative volatility of the both is increased, and the content of the vinyl acetate in the stream from which the ethyl acetate impurities are removed is reduced from 91% to 4%, so that the consumption of materials is significantly reduced. The adopted extractant is the acetic acid contained originally in the feed stream, and no new component is introduced, so that a task of treating the extractant in the system is not added after the separating efficiency is improved.

Equipment unspecified in the present disclosure is conventional equipment, and it can be achieved by adopting methods and equipment well known to those skilled in the art.

Although the present disclosure has been described with reference to specific implementation solutions and drawings, the present disclosure is not expected to be limited to the specific form here. On the contrary, the scope of the present disclosure is only limited by the appended claims. In addition, although independent features may be included in different claims, these features may be beneficially combined, and the inclusion in different claims does not mean that the combination of features is not feasible and/or advantageous. References to "first", "second," etc., do not exclude plurals.

What is claimed is:

1. A method for producing vinyl acetate, comprising a vinyl acetate synthesis process, a vinyl acetate refining process and a separation process of vinyl acetate and ethyl acetate; the vinyl acetate synthesis process mainly comprising an ethylene recovery tower (117), an acetic acid evaporator (103), an oxygen mixer (106), a vinyl acetate synthesis reactor (107), a first gas separating tower (108), a second gas separating tower (112) and a recycling gas compressor (101), all of which are sequentially connected, wherein the first gas separating tower (108) and the second gas separating tower (112) are connected with a degassing tank (113) and then sequentially connected with a recovered gas compressor (114), a water washing tower (115), an absorption tower (116) and a desorption tower (122); the vinyl acetate refining process mainly comprising an acetic acid tower (201), a crude VAC tower (202), and a fine VAC tower (203) which are sequentially connected, an aldehydo-ester concentration tower (204) and an acetaldehyde tower (205) which are sequentially connected to one branch at a top of the crude VAC tower (202), and a water phase receiving tank (207) and a dehydration tower (206) which are sequentially connected to one branch at a top of the acetic acid tower (201) and the other branch at the top of the crude VAC tower (202); and the vinyl acetate and ethyl acetate separation process mainly comprising an extracting and rectifying tower (401), an extracting and rectifying tower condenser (402), an extracting and rectifying tower supercooler (403), and an extracting and rectifying tower phase separator (404) which are sequentially connected, and an ethyl acetate tower (405), an ethyl acetate tower condenser (406), an ethyl acetate tower supercooler (407) and an ethyl acetate phase separator (408) which are sequentially connected to a kettle of the extracting and rectifying tower (401), wherein an extracting and rectifying process is adopted for the separation process of the vinyl acetate and ethyl acetate; wherein the extracting and rectifying process is adopted for the separation process of the vinyl acetate and the ethyl acetate, main equipment comprises the extracting and rectifying tower (401), the ethyl acetate tower (405), the extracting and rectifying tower condenser (402), the extracting and rectifying tower supercooler (403), the extracting and rectifying tower phase separator (404), the ethyl acetate tower condenser (406), the ethyl acetate tower supercooler (407) and the ethyl acetate tower phase separator (408); a top of the extracting and rectifying tower (401) is sequentially connected with the extracting and rectifying tower condenser (402), the extracting and rectifying tower supercooler (403) and the extracting and rectifying tower phase separator (404); two branches are arranged an oil phase outlet of the extracting and rectifying tower phase separator (404) and return to the extracting and rectifying tower (401) and the acetic acid tower (201) of the former system respectively, and a water phase outlet is connected with the water phase receiving tank (207); a tower kettle of the extracting and rectifying tower (401) is connected with the ethyl acetate tower (405), a top of the ethyl acetate tower (405) is sequentially connected with the ethyl acetate tower condenser (406), the ethyl acetate tower supercooler (407) and the ethyl acetate tower phase separator (408), a water phase outlet of the ethyl acetate tower phase separator (408) is connected with the ethyl acetate tower (405), and materials at an oil phase outlet are fed out of the system; and two branches are arranged at an outlet of a tower kettle of the ethyl acetate tower (405) and connected with the extracting and rectifying tower and the acetic acid tower (201) of the former system respectively; a stream containing acetic acid, vinyl acetate, water and ethyl acetate, which is extracted from the acetic acid tower (201) at sidelines, enters a middle of the extracting and rectifying tower (401), and the acetic acid is adopted as an extractant to be fed on an upper portion of the extracting and rectifying tower (401); and overhead vapor of the extracting and rectifying tower (401) mainly consists of vinyl acetate and water and also contains a trace amount of ethyl acetate not completely removed, condensate condensed by the extracting and rectifying tower condenser (402) enters the extracting and rectifying tower supercooler (403) to be further cooled and then fed to the extracting and rectifying tower phase separator (404) for phase separation, an oil phase part obtained after phase separation refluxes, the rest part is extracted and fed to the acetic acid tower (201) of the former system for treatment, and a water phase is fed to the dehydration tower (206) to recover organic matters therein.

2. The method according to claim 1, wherein a mixture containing ethyl acetate, a small amount of water and acetic acid in the tower kettle of the extracting and rectifying tower (401) enters the ethyl acetate tower (405) for rectifying; overhead vapor of the ethyl acetate tower (405) mainly consists of ethyl acetate and water and also contains a trace amount of vinyl acetate, condensate condensed by the ethyl acetate tower condenser (406) enters the ethyl acetate tower supercooler (407) to be further cooled and then fed to the ethyl acetate tower phase separator (408) for phase separation, a water phase obtained after phase separation refluxes, and an oil phase is discharged out of the system as an ethyl acetate impurity stream; and a main component in the tower kettle of the ethyl acetate tower (405) is acetic acid, one part returns to the extracting and rectifying tower (401) as the extractant, and the rest part returns to the acetic acid tower (201) of the former system for feeding.

3. The method according to claim 1, wherein the acetic acid is adopted as the extractant in the separation process of the vinyl acetate and the ethyl acetate by adopting the extracting and rectifying process, and the extractant is added from the upper portion of the extracting and rectifying tower (401).

4. The method according to claim 3, wherein a ratio of mass flow of the extractant of acetic acid to mass flow of feed extracted from the acetic acid tower (201) at the sidelines is 0.2-2:1.

5. The method according to claim 4, wherein the ratio of mass flow of the extractant of acetic acid to mass flow of the feed extracted from the acetic acid tower (201) at the sidelines is 1.2:1.

* * * * *